United States Patent
Zeelie

(10) Patent No.: US 10,465,121 B2
(45) Date of Patent: Nov. 5, 2019

(54) PROCESSING CARBONACEOUS MATERIALS

(71) Applicant: Nelson Mandela Metropolitan University, Port Elizabeth (ZA)

(72) Inventor: Bernard Zeelie, Port Elizabeth (ZA)

(73) Assignee: NELSON MANDELA METROPOLITAN UNIVERSITY, Port Elizabeth (ZA)

(*) Notice: Subject to any disclaimer, the term of this patent is extended or adjusted under 35 U.S.C. 154(b) by 149 days.

(21) Appl. No.: 15/038,301

(22) PCT Filed: Nov. 19, 2014

(86) PCT No.: PCT/IB2014/066151
§ 371 (c)(1),
(2) Date: May 20, 2016

(87) PCT Pub. No.: WO2015/075639
PCT Pub. Date: May 28, 2015

(65) Prior Publication Data
US 2016/0289567 A1    Oct. 6, 2016

(30) Foreign Application Priority Data

Nov. 20, 2013 (ZA) .................. 2013/08726

(51) Int. Cl.

| | | |
|---|---|---|
| *C10B 53/02* | (2006.01) | |
| *C10L 5/04* | (2006.01) | |
| *C10L 5/44* | (2006.01) | |
| *C10G 32/00* | (2006.01) | |
| *C10B 53/04* | (2006.01) | |
| *C10B 57/08* | (2006.01) | |
| *C12N 1/12* | (2006.01) | |

(52) U.S. Cl.
CPC .............. *C10B 53/02* (2013.01); *C10B 53/04* (2013.01); *C10B 57/08* (2013.01); *C10G 32/00* (2013.01); *C10L 5/04* (2013.01); *C10L 5/442* (2013.01); *C10L 5/445* (2013.01); *C12N 1/12* (2013.01); *Y02E 50/10* (2013.01); *Y02E 50/14* (2013.01); *Y02E 50/30* (2013.01)

(58) Field of Classification Search
CPC ........... C10B 53/02; C10B 53/04; C10G 1/02; C10L 5/04; C10L 5/44; C10L 5/442; C10L 5/445
See application file for complete search history.

(56) References Cited

U.S. PATENT DOCUMENTS 8,916,043 B2   12/2014   Charon et al.

FOREIGN PATENT DOCUMENTS

| JP | 3028498 B2 | 4/2000 |
|---|---|---|
| JP | 2011251782 A | 12/2011 |
| WO | 2010099550 A1 | 9/2010 |
| WO | 2012025806 A1 | 3/2012 |
| WO | 2013142619 A1 | 9/2013 |

OTHER PUBLICATIONS

International Search Report and Written Opinion issued in corresponding International Application No. PCT/IB2014/066151, dated Mar. 10, 2015.

*Primary Examiner* — Renee Robinson
(74) *Attorney, Agent, or Firm* — Andrus Intellectual Property Law, LLP

(57) ABSTRACT

A method of processing a carbonaceous material in the form of carbonaceous fines is provided in which the carbonaceous material is treated with micro-algae to adsorb the micro-algae onto the carbonaceous material followed by heating in a heat activating step. Such heating is effected to a temperature within the range of from that at which water starts evaporating to a temperature at which volatile components of the carbonaceous material start to volatilize. The heating is continued for a duration selected to allow chemical interaction between the micro-algae and the carbonaceous material so as to alter the chemical structure of the carbonaceous material. The carbonaceous material microalgae are preferably in the form of substantially intact cells that are still in a photosynthetically active state. Dry carbonaceous materials may be mixed with micro-algae slurry in water, or micro-algae may be added to carbonaceous material already present in water.

11 Claims, 3 Drawing Sheets

PROCESSING CARBONACEOUS MATERIALS

CROSS-REFERENCE TO RELATED APPLICATIONS

This application is the U.S. national stage application of International Application PCT/IB2014/066151, filed Nov. 19, 2014, which international application was published on May 28, 2015, as International Publication WO2015/075639 in the English language. The international application is incorporated herein by reference, in entirety. The international application claims priority to South African Patent Application No. ZA 2013/08726, filed Nov. 20, 2013, which is incorporated herein by reference, in entirety.

FIELD OF THE INVENTION

This invention relates to the processing of carbonaceous materials and more particularly the thermochemical processing of carbonaceous materials by a process that includes the treatment of such materials with microalgae. In this specification the term thermochemical processing is intended to include, but is not limited to, such processes as pyrolysis, distillation, gasification, coking, liquefaction and combustion.

The carbonaceous materials may be of any origin but are most typically fossil fuels such as coal, charcoal and crude oil.

BACKGROUND TO THE INVENTION

The conversion of carbonaceous materials into energy and other products often involves a thermochemical conversion step. In the production of energy, carbonaceous materials may for example be combusted to generate heat.

Alternatively, carbonaceous materials may be converted into other products through thermochemical processing. Examples include the conversion of coal into fuels by means of gasification followed by further chemical reaction of the resultant gas mixture comprising carbon monoxide and hydrogen.

Alternatively coal may be liquefied by heating at high temperature and pressure in the presence of catalysts and a hydrogen-transfer solvent to produce liquid products directly.

Coking coal is produced via the pyrolysis of coal under inert conditions or vacuum to produce essentially three products: a gaseous product, a liquid product (pyrolysis oil), and a solid product (coking coal). The latter process is normally carried out at very high temperatures (>1000° C.). In a variant of the latter process, pyrolysis may be carried out at moderate temperatures (~600° C.) to produce pyrolysis oil and a partially de-volatilized coal.

Crude oil, on the other hand, is normally subjected to an initial high temperature distillation process in order to separate the oil into different boiling point fractions. Such distillation processes generally generate four crude products, namely a top fraction containing all the lowest boiling components; a middle fraction which contains components with medium boiling points; a heavy fraction (high boiling points); and a bottom fraction that cannot be distilled.

To date there is little that can be done to change the properties of materials such as coal, charcoal and crude oil with the view to improve the thermochemical processing of such materials to provide improved yields or improved product properties. As an example, during the distillation of crude oil, the nature of the crude oil typically determines the relative proportions of the basic products.

Our earlier international patent application publication number WO 2012/025806 discloses that fine coal and other carbonaceous material may conveniently be rendered usable by agglomeration using microalgae biomass as binder for fine carbon particles. This work with microalgae and carbonaceous material has led to further processes being developed as will be further described below.

In this specification the term coal or carbonaceous fines should generally be interpreted to mean sub 250 micron particle sizes. It is however preferred that the particle size actually to be sub 150 micron for the more efficient operation of the invention as will become more apparent from what follows.

SUMMARY OF THE INVENTION

In accordance with this invention there is provided a method of processing a carbonaceous material in the form of carbonaceous fines comprising treating the carbonaceous material with micro-algae so that the micro-algae adsorbs onto the carbonaceous material, and heating the carbonaceous material with the adsorbed microalgae in a heat activating step to a temperature within the range from a temperature at which water starts evaporating to a temperature at which volatile components of the carbonaceous material start to volatilize with the heating being continued for a duration selected to allow chemical interaction between the micro-algae and the carbonaceous material so as to alter the chemical structure of the carbonaceous material.

A further feature of the invention provides for the microalgae to be in the form of substantially intact cells that are preferably still in a photosynthetically active state. It is thus preferred that freshly harvested microalgae that have been harvested or concentrated by means of a mechanism that does not result in cell rupture be used. In order to facilitate adsorption of microalgae onto the carbonaceous material contacting between the micro-algae and the carbonaceous material may be done either by mixing dry carbonaceous materials such as coal or charcoal with micro-algae slurry in water, or by adding micro-algae as a wet filter or centrifuge cake to the carbonaceous material that is already present in water such as coal fines leaving a coal processing plant. The micro-algae in the form of a wet filter or centrifuge cake may, of course, be added to a liquid carbonaceous material such as a crude oil or tar. Contacting is preferably carried out in a manner aimed at loading the carbonaceous material evenly with micro-algae adsorbed thereon in a preferred amount of from 5 to 15% by weight of the carbonaceous material.

Clearly, the temperature range within which the heat activating step takes place will depend on the nature and composition of the carbonaceous material and may vary from one carbonaceous material to another.

In one instance the carbonaceous material was in the form of coal fines and at the ambient conditions the lower temperature was effectively about 80° C. whilst volatiles started coming off from a temperature of about 150° C. In that instance a preferred narrower temperature range would be from about 100 to about 130° C. with an indicated optimum being about 110° C.

The duration for which the heat activating step is carried out depends on the temperature and other physical characteristics of the carbonaceous material with micro-algae adsorbed thereon with a higher temperature typically requiring a shorter time and a lower temperature requiring a longer time. In this particular instance the duration of the heat activating step was from 0.5-3 hours and conveniently 1-2 hours. In any event, the heat activating step is preferably carried out until the carbonaceous material has a moisture content of not more than about 10 mass %.

When using a slurry of micro-algae in water, the micro-algae may be present in any concentration that would enable subsequent mixing with the carbonaceous materials. Typically, microalgae concentrations may vary from about 1 gram/litre to 10 grams/litre if taken directly from commercial growth systems. Alternatively, a wet cake of micro-algae, typically containing between 30 to 200 g/Kg of micro-algae, may be used to mix with a liquid carbonaceous material, or carbonaceous material slurry.

Microalgae will most typically be derived from commercial cultivation systems such as a photo-bioreactor, pond, or raceway system, in which instance the contact constitutes harvesting of microalgae in a manner that will preserve the integrity of the harvested microalgae cells. For the invention to function optimally, it is preferred that microalgae cells are not broken during any processing step such as harvesting and that the microalgae cells are contacted with the coal fines as whole, or intact cells.

In order that the invention may be more fully understood, different embodiments thereof will now be described with reference to the accompanying drawings.

DETAILED DESCRIPTION WITH REFERENCE TO THE DRAWINGS

Figure 1:
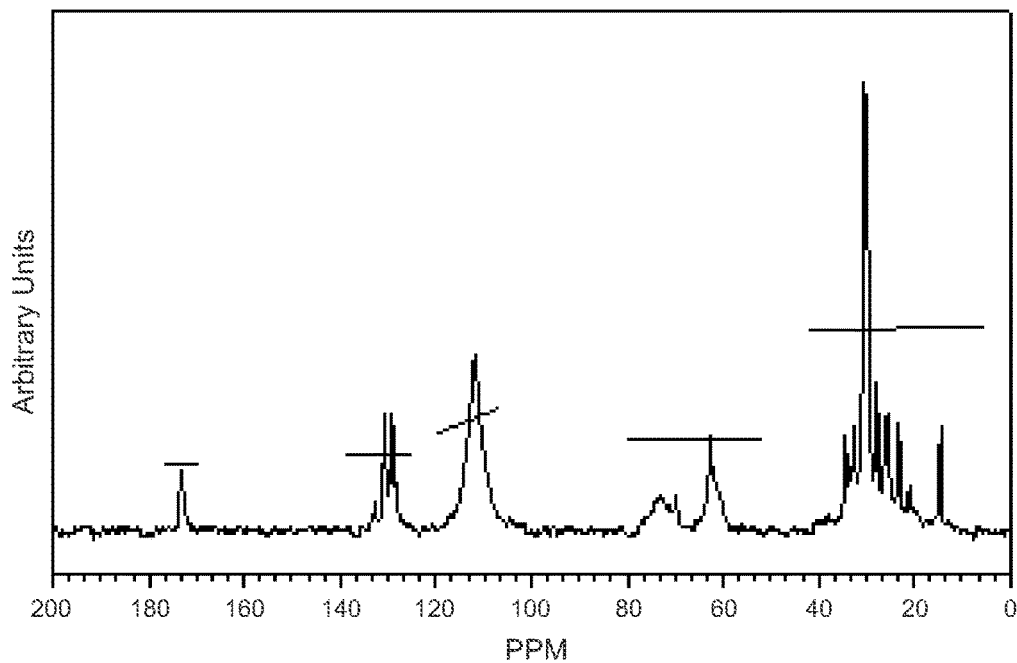
FIG. 1 shows the solid state NMR spectrum ($^{13}$C Onepulse) of the micro-algae biomass.
Figure 2:
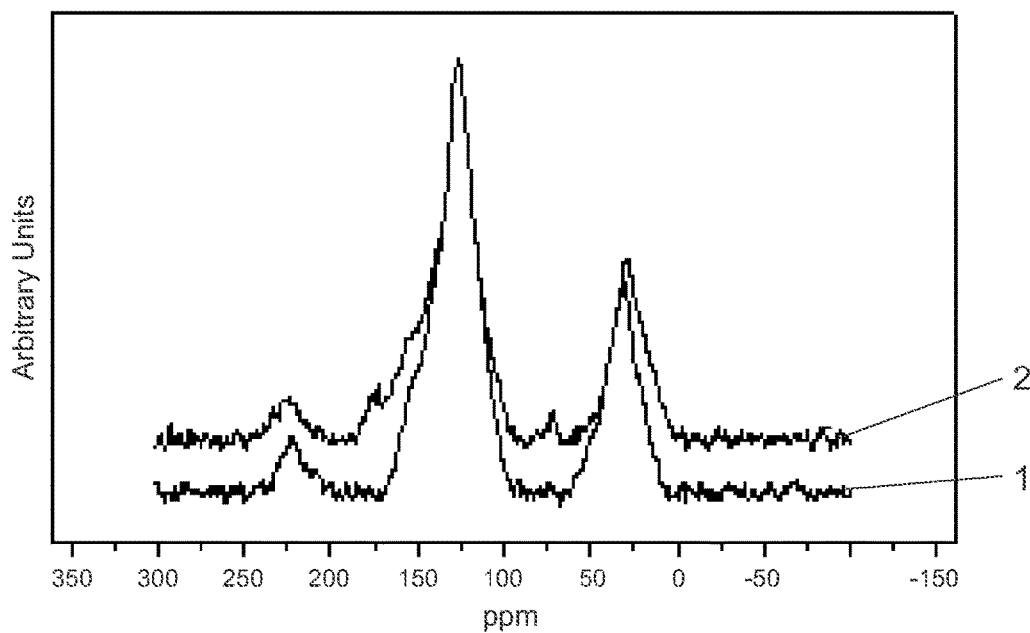
FIG. 2 shows a comparison between the solid state NMR spectra ($^{13}$C CP-MAS) of coal and of the coal—micro-algae composite after heat activation.

Solid state NMR studies were carried out on a particular coal sample in the form it was received and the same coal was modified by the adsorption of 10 mass % (dry-weight basis) micro-algae, followed by heating at 105° C. for two hours. The solid state NMR spectra of the two different materials are shown in FIGS. 1 and 2 with the spectra for coal being indicated by numeral (1) in FIG. 2 and that for the coal-micro-algae agglomerate being indicated by numeral (2). Subsequent calculation of structural parameters are summarized in Table 1 below (refer to Mark S. Solum, Ronald J. Pugmire, and David M. Grant, $^{13}$0 Solid-state NMR of Argonne Premium Coals, Energy & Fuels 1989, 3, 187-193 for details) and clearly indicate that the adsorption of micro-algae onto finely divided coal and subsequent heating at 105° C. results in significant structural changes within the coal sample.

In Table 1, column 1 lists the various structural parameters of coals that may be derived from the information obtained by $^{13}$C solid state NMR (symbols in column 2). Column 3 lists the values of these parameters for the coal sample. Column 4 lists the values for the coal-micro-algae agglomerate. Column 5 gives an estimate of the magnitude of the experimental error present in the estimations and may be used to determine whether a particular difference between the parameter values for coal and coal-micro-algae is real or just error; for a particular difference to be real, the difference between the two parameter values must exceed the estimated experimental error. Columns 6 and 7 list parameter values for two typical types of coal as a way to illustrate the main differences between the coal-micro-algae agglomerate and coals in general.

From the comparisons listed in Table 1, it may be observed that micro-algae results in the largest changes to those parameters that appears in rows # 8, 9, 10, 13, 14, 15, and 16. A person skilled in the art may find it obvious that the results suggest that the effect of micro-algae bonding to fine coal particles causes the structure of the coal to become simplified in the sense that the large clusters of aromatic rings found within the coal structure are in some way split so that there are more, and smaller, clusters with fewer linkages between clusters of aromatic rings. In addition, the degree of protonation of the aromatic rings is increased.

TABLE 1

| # | 1 | 2 | 3 Fine Coal | 4 Coal&Algae mix | 5 stdev$^{Pugmire}$ | 6 Inertinite rich coal | 7 vitrinite rich coal |
|---|---|---|---|---|---|---|---|
| 1 | Fraction Aromatics | $f_a$ | 0.79 | 0.80 | 0.03 | 0.68 | 0.66 |
| 2 | Corrected Fraction Aromatics (excl CO) | $f_a^*$ | 0.79 | 0.75 | 0.04 | 0.68 | 0.64 |
| 3 | Fraction Aliphatics | $f_{al}$ | 0.21 | 0.20 | 0.02 | 0.32 | 0.34 |
| 4 | Fraction Aliphatic C's bonded to Oxygen | $f_{al}^O$ | 0.00 | 0.01 | 0.02 | 0.00 | 0.00 |
| 5 | Fraction CO | $f_a^{CO}$ | 0.00 | 0.04 | 0.02 | 0.01 | 0.02 |
| 6 | Fraction Phenolics | $f_a^P$ | 0.06 | 0.09 | 0.02 | 0.07 | 0.08 |
| 7 | Fraction Alkylated Aromatics | $f_a^S$ | 0.17 | 0.17 | 0.03 | 0.16 | 0.16 |
| 8 | Fraction Non-Protonated C's in aromatic region | $f_a^N$ | 0.55 | 0.46 | 0.03 | 0.51 | 0.46 |
| 9 | Fraction Protonated C's in aromatic region | $f_a^H$ | 0.24 | 0.29 | 0.03 | 0.17 | 0.18 |
| 10 | Fraction Bridgehead C's | $f_a^B$ | 0.31 | 0.20 | 0.04 | 0.28 | 0.23 |
| 11 | Fraction Non-Protonated C's + Methyl groups in Aliphatic region | $f_{al}^{N*}$ | 0.00 | 0.00 | 0.03 | 0.07 | 0.08 |

TABLE 1-continued

| # | 1 | 2 | 3 Fine Coal | 4 Coal&Algae mix | 5 stdev$^{Pugmire}$ | 6 Inertinite rich coal | 7 vitrinite rich coal |
|---|---|---|---|---|---|---|---|
| 12 | Aliphatic CH + CH2 | $f_{al}^H$ | 0.21 | 0.20 | 0.02 | 0.24 | 0.26 |
| 13 | Mole fraction of Aromatic Bridgehead C's | $X_b$ | 0.39 | 0.27 | 0.06 | 0.41 | 0.35 |
| 14 | Average # of Aromatic C's per cluser | C | 19.3 | 14.1 | 3.00 | 20.31 | 17.65 |
| 15 | #Clusters/100 | | 4.10 | 5.35 | | 3.36 | 3.65 |
| 16 | #of attachments per cluster | σ + 1 | 5.80 | 4.83 | | 6.80 | 6.52 |

The observations and conclusions described above led to the proposal that the adsorption of micro-algae onto fine coal particles followed by heating at relatively low temperatures typically in the range 105-150° C. so as not to drive off combustible volatile materials results in the formation of a coal-micro-algae agglomerate in which the chemical structure is different from both the constituent coal and the micro-algae constituents. In addition, it is postulated that this agglomerate will behave as a single substance under thermochemical processing conditions such as combustion, unlike what is typically observed for coal and biomass mixtures (as for example described by M. V. Gil, D. Cascal, C. Previda, J. J. Pis, and F. Rubiera, "Thermal behaviour and kinetics of coal/biomass blends during co-combustion", Bioresource Technology, 101 (2010), 5601-5608; and C. Wang, F. Wang, Q. Yang, and R. Liang, "Thermogravimetric studies of the behaviour of wheat straw with added coal during combustion", Biomass and Bioenergy, 33 (2009), 50-56) where the coal and biomass constituents give rise to thermal events traceable to either the biomass or coal constituent.

Figure 3:
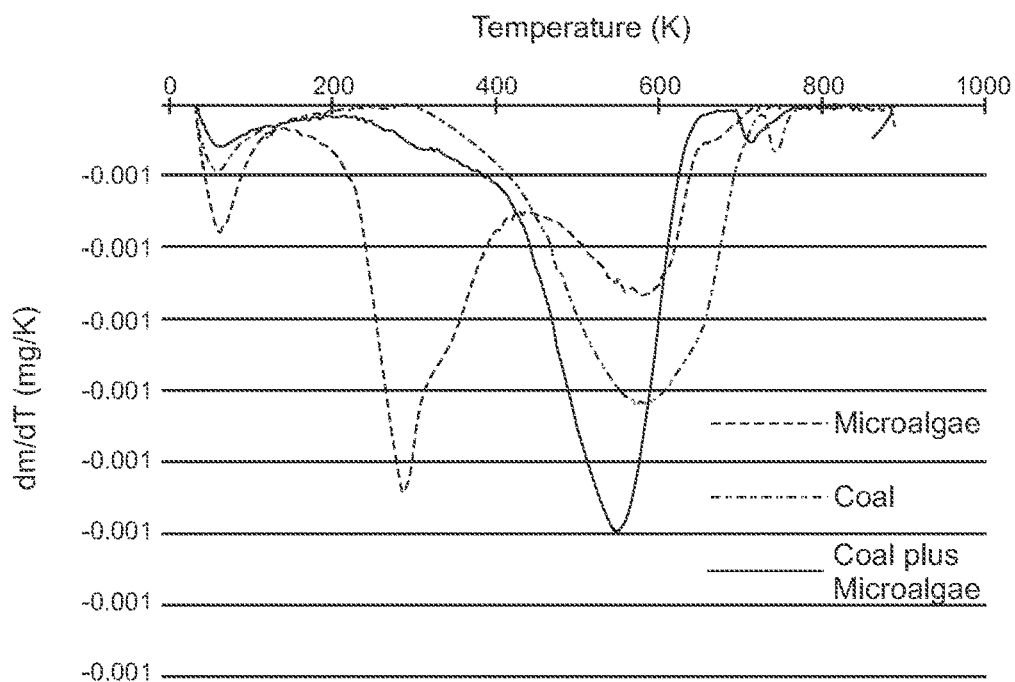
FIG. 3 shows the derivative thermogravimetric combustion profiles for coal, the micro-algae, and the coal-micro-algae composite after heat activation.
Figure 4:
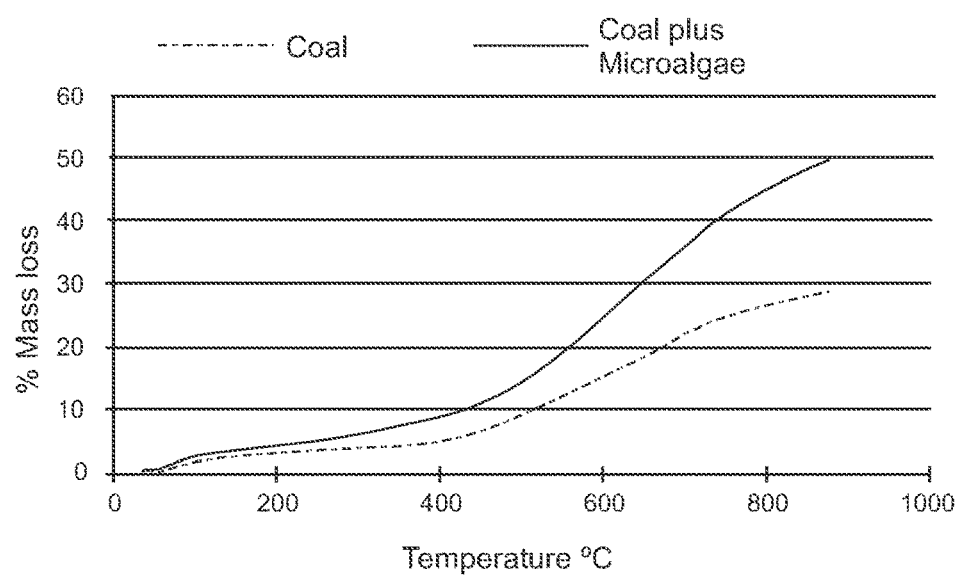
FIG. 4 shows the pyrolysis profile for coal and the coal-microalgae composite after heat activation; and, FIG. 5 shows the temperature profile for the combustion of coal and coal-micro-algae composite under identical conditions.

To test the hypothesis regarding the behaviour of the coal-micro-algae agglomerates or composites under thermochemical processing conditions, coal and coal-micro-algae composites were subjected to both combustion conditions with heating under oxygen atmosphere and pyrolysis conditions with heating under an inert atmosphere. The results of these tests are depicted in FIGS. 3 and 4, respectively. FIG. 3 shows the derivative thermogravimetric behaviour of micro-algae, coal, and an agglomerate/composite of coal and micro-algae containing 10 mass % of micro-algae (dry weight basis). It can be seen that the combustion profile for the micro-algae biomass is considerably more complex than that of coal. Both materials show an initial loss of moisture (<~150° C.) followed by either four (micro-algae) or two (coal) combustion events. This difference in behaviour may be traced directly to the significantly higher volatile content of the micro-algae biomass compared to coal and consequently a lower amount of fixed carbon. The behaviour of the coal-micro-algae agglomerate/composite resembles the combustion behaviour of coal with no evidence of a separate combustion event due to the large volatile content of the micro-algae. In addition, the entire combustion process is shifted to a lower peak combustion temperature, but with a significantly increased combustion intensity as indicated by the increased rate of combustion for the composite.

The pyrolysis profiles for coal and micro-algae composite that were prepared from the same coal and using a 10 mass % micro-algae loading (dry weight basis) in FIG. 4 show that the total mass loss for the pure coal of ~28 mass % at 900° C. corresponds closely to the volatile content of the coal as determined by standard tests being ASTM methods D_3172-D_3175. For the coal-micro-algae agglomerate/composite, however, the total mass loss is increased to ~50 mass %, significantly more than what could be expected from the linear sum (32.36%) of the volatile contents of the original coal (27.56%) and the micro-algae biomass (75.59%).

The difference between coal and the same coal treated with 10% microalgae (w/w %) was further tested under mild pyrolysis conditions but subjecting coal or coal-microalgae composites to pyrolysis under a nitrogen atmosphere at a temperature of 450° C. The results of these tests are summarized in Table 2 below. These results clearly show that under real life pyrolysis conditions, the amount of volatile products (gas and liquid) is increased significantly when coal is modified with microalgae prior to the pyrolysis step.

TABLE 2

| Run | Total Mass in (g) | Char out (g) | Ash content (%) | Mass loss (% - Ash-free) |
|---|---|---|---|---|
| Coal | 800.17 | 682.19 | 21.02% | 18.67% |
| Coal-algae 1 | 600.18 | 483.9 | 21.02% | 24.53% |
| Coal-algae 2 | 600.2 | 480.88 | 21.02% | 25.17% |
| Coal-algae 3 | 617.68 | 503.64 | 21.02% | 23.38% |
| Coal-algae 4 | 662.19 | 536.08 | 21.02% | 24.11% |
| Coal-algae 5 | 660.95 | 536.18 | 21.02% | 23.90% |
| Total (Coal-algae) | 3141.2 | 2540.68 | 21.02% | 24.21% |
| Total liquid out (Coal-algae) | | 425.79 | 17.16% | |
| Gas (by difference) | | 174.73 | 7.04% | |

These results from the combustion and pyrolysis tests strongly suggest that the hypotheses that the micro-algae change the chemical structure of the coal, and that this change would change the behaviour under thermochemical processing conditions are correct.

Figure 5:
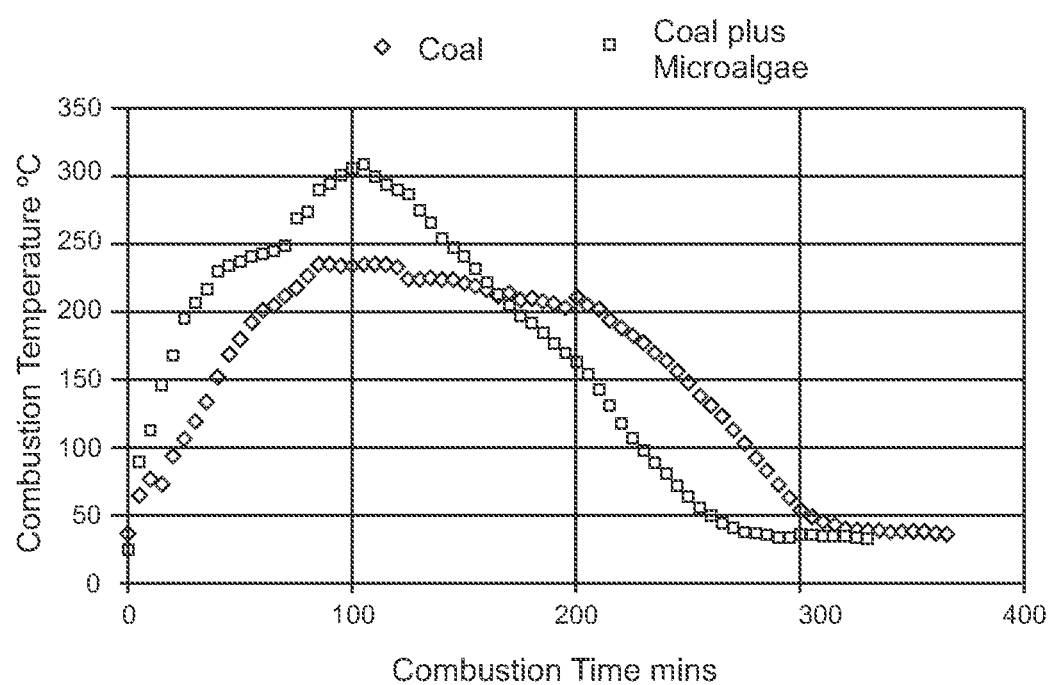

The hypotheses were further tested by first comparing the combustion of coal with the combustion of a coal-micro-algae agglomerate/composite produced from the same coal. FIG. 5 shows the variation in temperature measured at a fixed distance above a combustion bed for the combustion of equal amounts of coal and coal-micro-algae agglomerate/composite and using natural air flow through the combustion bed. The peak combustion temperature recorded during the combustion of the coal-micro-algae agglomerate/composite was significantly higher than that recorded for the combustion of the coal (some 70° C.). In addition, the peak temperature is reached before the peak temperature for coal, and burn-out is also significantly faster for the coal-micro-algae agglomerate/composite.

It is envisaged that there will be numerous carbonaceous materials to which the invention can be applied with good effect.

The invention claimed is:

1. A method of modifying a carbonaceous material comprising:

contacting the carbonaceous material in the form of carbonaceous fines of sub 250 micron particle size with an aqueous suspension of microalgae in the form of substantially intact cells to form an aqueous suspension of the microalgae adsorbed onto the carbonaceous material; and altering the chemical structure of the carbonaceous material by heating the aqueous suspension of the carbonaceous material with the adsorbed substantially intact cells of microalgae in a heat activating step to a selected temperature that depends on the nature and composition of the carbonaceous material and that is within the range from a lower temperature at which water starts evaporating to a higher temperature at which volatile components of the carbonaceous material start to volatilize with the heating being continued for a duration selected to allow chemical interaction between the microalgae in the form of substantially intact cells and the carbonaceous material so as to alter the chemical structure of the carbonaceous material;

wherein said contacting is carried out in a manner aimed at loading the carbonaceous material evenly with microalgae adsorbed thereon in an amount of from 5 to 15% by weight of the carbonaceous material; and wherein the lower temperature is about 80° C. and the higher temperature is about 150° C.

2. A method of modifying a carbonaceous material as claimed in claim 1 in which the microalgae are still in a photosynthetically active state.

3. A method of modifying a carbonaceous material as claimed in claim 1 in which the microalgae have been harvested or concentrated by means of a mechanism that does not result in cell rupture.

4. A method of modifying a carbonaceous material as claimed in claim 1 in which the contacting between the micro-algae and the carbonaceous material is done either by mixing dry carbonaceous materials with micro-algae slurry in water, or by adding micro-algae as a wet filter or centrifuge cake to the carbonaceous material that is already present in water.

5. A method of modifying a carbonaceous material as claimed in claim 4 in which the microalgae are provided at a concentration in water from about 1 gram/litre to 10 grams/litre.

6. A method of modifying a carbonaceous material as claimed in claim 1 in which the temperature range is from about 100 to about 130° C.

7. A method of modifying a carbonaceous material as claimed in claim 1 in which the duration of the heat activating step is from 0.5-3 hours.

8. A method of modifying a carbonaceous material as claimed in claim 1 in which the duration of the heat activating step is from 1-2 hours.

9. A method of modifying a carbonaceous material as claimed in claim 1 in which the heat activating step is carried out until the carbonaceous material has a moisture content of not more than about 10 mass %.

10. A method of modifying a carbonaceous material as claimed in claim 1 in which a wet cake of micro-algae containing between 300 to 700 g/Kg of micro-algae is used to mix with a liquid carbonaceous material, or carbonaceous material slurry.

11. A method of modifying a carbonaceous material as claimed in claim 1 in which the carbonaceous fines have a particle size of sub 150 micron.

* * * * *